(12) United States Patent
Grajcar

(10) Patent No.: US 8,863,435 B2
(45) Date of Patent: Oct. 21, 2014

(54) ARCHITECTURE FOR SYMBIOTIC LIVESTOCK AND BIOFUEL PRODUCTION

(75) Inventor: Zdenko Grajcar, Crystal, MN (US)

(73) Assignee: Once Technologies, Inc., Plymouth, MN (US)

( * ) Notice: Subject to any disclaimer, the term of this patent is extended or adjusted under 35 U.S.C. 154(b) by 76 days.

(21) Appl. No.: 13/189,807

(22) Filed: Jul. 25, 2011

(65) Prior Publication Data

US 2012/0279119 A1 Nov. 8, 2012

Related U.S. Application Data

(60) Provisional application No. 61/367,468, filed on Jul. 26, 2010.

(51) Int. Cl.
| | | |
|---|---|---|
| *A01G 7/00* | (2006.01) | |
| *C11B 1/00* | (2006.01) | |
| *C12M 1/00* | (2006.01) | |

(52) U.S. Cl.
CPC ............... *C12M 43/00* (2013.01); *C11B 1/00* (2013.01); *C12M 43/02* (2013.01); *C12M 21/02* (2013.01)
USPC .......................................................... 47/1.4

(58) Field of Classification Search
USPC ......... 119/226, 247; 47/17; 435/257.1–257.6, 435/262.5, 300.1
See application file for complete search history.

(56) References Cited

U.S. PATENT DOCUMENTS

| | | | | |
|---|---|---|---|---|
| 3,521,400 A | * | 7/1970 | Ort ................................... | 47/1.4 |
| 3,645,040 A | * | 2/1972 | Ort ................................... | 47/1.4 |
| 3,732,089 A | * | 5/1973 | Megronigle ........................ | 71/8 |
| 3,955,318 A | * | 5/1976 | Hulls ................................ | 47/1.4 |
| 4,267,038 A | * | 5/1981 | Thompson .................... | 210/602 |
| 5,097,795 A | * | 3/1992 | Adey ............................ | 119/262 |
| 5,820,759 A | * | 10/1998 | Stewart et al. ................ | 210/602 |
| 6,146,507 A | * | 11/2000 | Gustafson ................... | 204/275.1 |
| 6,470,828 B1 | * | 10/2002 | Townsend et al. ............. | 119/447 |
| 6,698,383 B1 | * | 3/2004 | Terwort et al. ................ | 119/451 |
| 2008/0050800 A1 | * | 2/2008 | McKeeman et al. ........ | 435/262.5 |
| 2009/0215155 A1 | | 8/2009 | Cloud et al. | |
| 2009/0227003 A1 | * | 9/2009 | Blotsky et al. ............. | 435/257.1 |
| 2009/0301399 A1 | | 12/2009 | Brown et al. | |
| 2010/0151558 A1 | | 6/2010 | Alianell et al. | |

OTHER PUBLICATIONS

Joseph C. Dodd, Algae Production and Harvesting From Animal Wastewaters, Agricultural Wastes (1) (1979), pp. 23-37.*
International Preliminary Report on Patentability issued in International Patent Application No. PCT/US2011/045171 dated Feb. 7, 2013.

* cited by examiner

*Primary Examiner* — Rob Swiatek
*Assistant Examiner* — Ebony Evans
(74) *Attorney, Agent, or Firm* — McDermott Will & Emery LLP

(57) ABSTRACT

Methods and apparatus involve locating an algae production facility in close proximity to a livestock production facility whereby the outputs of one or both facilities promotes productivity levels in the facility. In an illustrative example, the algae production facility includes a bioreactor in fluid communication with the atmosphere inside, for example, a poultry facility. In some examples, the atmosphere inside the poultry facility may be around a substantially controlled temperature suitable for poultry. The atmosphere may further contain substantial Nitrogen-content suitable to promote algae growth. Various embodiments may symbiotically consume waste products from each facility to promote production of, for example, protein for food and algae, which may be used for animal feed, for example, and/or processed into fuel. In some examples, the algae production facility may be conveniently packaged into a module. In some examples, the module may be stored and shipped in a conventional shipping container.

16 Claims, 3 Drawing Sheets

US 8,863,435 B2

ARCHITECTURE FOR SYMBIOTIC LIVESTOCK AND BIOFUEL PRODUCTION

This application claims the benefit of U.S. Provisional Patent Application Ser. No. 61/367,468, filed by Grajcar, Z. on Jul. 26, 2010, entitled "Architecture for Symbiotic Livestock and Biofuel Production," the entire contents of which are incorporated herein by reference.

TECHNICAL FIELD

Various embodiments relate to apparatus and methods for generating biofuels.

BACKGROUND

Modern societies have developed various processes to transform energy into useful work driven by various types of fuels. For example, gasoline may be ignited to drive pistons that deliver torque to the wheels of a car. Fossil fuels, for example, coal, may be consumed in large quantities in many electric power plants that distribute electric power over large transmission networks. Other fuel sources may be used to generate useful mechanical, electrical, or other type of work.

A class of fuels that may be new to fossil fuels may be referred to as a biofuel. Biofuel may be generally understood as including a type of fuel that is generated from biomass. Biomass may generally be considered biological matter from living or recently living organisms that can serve as an energy source. Examples of biomass may sometimes include waste, wood, gas, and alcohol. Concern over increasing oil prices, energy security, greenhouse gas emissions from fossil fuels, and government subsidies has garnered increased interest in biofuels.

SUMMARY

Methods and apparatus involve locating an algae production facility in close proximity to a livestock production facility whereby the outputs of one or both facilities promotes productivity levels in the other facility. In an illustrative example, the algae production facility includes a bioreactor in fluid communication with the atmosphere inside, for example, a poultry facility. In some examples, the atmosphere inside the poultry facility may be around a substantially controlled temperature suitable for poultry. The atmosphere may further contain substantial Nitrogen-content suitable to promote algae growth. Various embodiments may symbiotically consume waste products from each facility to promote production of, for example, protein for food and algae, which may be used for animal feed, for example, and/or processed into fuel. In some examples, the algae production facility may be conveniently packaged into a module. In some examples, the module may be stored and shipped in a conventional shipping container.

Certain embodiments of a system for symbiotic livestock and biofuel production may achieve one or more advantages. For example, release of noxious waste gasses such as ammonia may be beneficially reduced and converted to stimulating a renewable energy source based on algae. Some embodiments may advantageously capture available kinetic airflow, heat, carbon dioxide, ammonia, and various nutrients from livestock excretions that are normally discarded and may recycle those energies and nutrients by redirecting them to grow algae. Consequently, the overall effect of each installation may be to incrementally reduce noxious gas emissions, recapture waste heat and kinetic energy, and reduce the production cost of a valuable renewable fuel source. The algae production may generate oxygen and/or feed, for example, that can be redirected to enhance the atmosphere inside the poultry facility, which may promote the health and well-being of poultry being raised as a protein food source.

In one exemplary aspect, an embodiment provides a system for producing algae cells for use in processing biofuel which comprises a livestock production facility for generating livestock output from their consumption of feed and water, an algae production facility located proximate to the livestock production facility, the algae production facility comprising a reaction chamber for growing algae cells using livestock output and a conduit providing fluid connection between the livestock production facility and the algae production facility, the conduit defining a passageway comprising an input port through which livestock output is received from the livestock production facility and an output port through which livestock output is discharged into the reaction chamber. A system in the sense of the embodiment is a facility that comprises further facilities. The system can further comprise means for transferring livestock output from the livestock production facility into the algae production facility through the conduit. The system can further comprise means for drying algae after being interacted with livestock output to obtain at least partially dried biomass with substantial oil content. The livestock output can comprise manure, ammonia, carbon dioxide, heat and/or kinetic airflow. The system can also comprise means for supplying energy to the system. In the system at least a portion of the algae production facility can be located within the livestock production facility. The system can comprise a means for conveying algae output from the algae production facility into the livestock production facility. The means for conveying algae output from the algae production facility into the livestock production facility can comprise a second conduit connecting the livestock production facility and the algae production facility. The system can further comprise a housing for storing and shipping the algae production facility, wherein the housing comprises a shipping container. The algae output can comprise oxygen.

In another exemplary aspect, an embodiment also provides a method for producing algae cells for use in processing biofuel, the method comprising providing a system comprising a livestock production facility for generating livestock output from their consumption of feed and water, an algae production facility located proximate to the livestock production facility that comprises a reaction chamber for growing algae cells using livestock output, and a conduit connecting the livestock production facility and the algae production facility defining a passageway comprising an input port through which livestock output is received from the livestock production facility and an output port through which livestock output is discharged into the reaction chamber; introducing feed and water into the livestock production facility; generating livestock output based on livestock consumption of feed and water; and, introducing livestock output into the reaction chamber through the conduit to promote the growth of algae cells. The method can further comprise drying algae after being interacted with livestock output to obtain at least partially dried biomass with substantial oil content. The method can further comprise introducing output from the growth of algae cells from the algae production facility into the livestock production facility. The method can further comprise processing the biomass into a fuel. The method can further comprise capturing the kinetic airflow available in the livestock production facility to supply energy to operate the algae production facility. The method can further comprise capturing the kinetic airflow further comprises generating electrical power to operate the algae production facility.

The details of various embodiments are set forth in the accompanying drawings and the description below. Other features and advantages will be apparent from the description and drawings, and from the claims.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION OF ILLUSTRATIVE EMBODIMENTS

Figure 1:
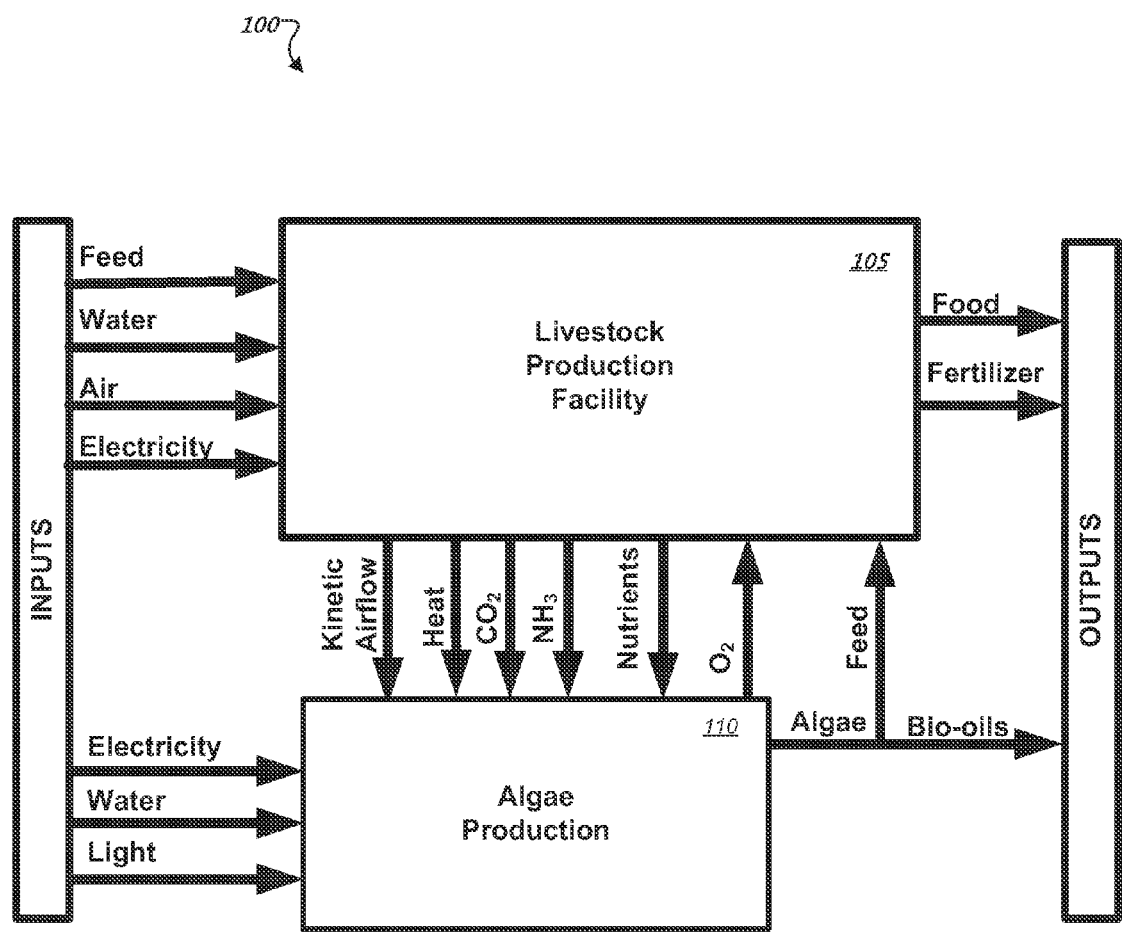
FIG. 1 shows a block diagram architecture for an exemplary integrated facility for producing livestock and biologically-derived fuels in a symbiotic manner.

FIG. 1 shows a block diagram architecture for an exemplary integrated facility for producing livestock and biologically-derived fuels in a symbiotic manner.

Biologically-derived fuels, as used herein, generally may be referred to as bio-fuels.

As depicted in FIG. 1, an integrated facility 100 includes a livestock production facility 105 located in close proximity to an algae production module 110. Each of the facilities 105, 110 may require certain inputs and yields certain outputs.

In the depicted example, the algae production module 110 receives electricity, water, and light from external sources, and further receives kinetic airflow, heat (e.g., in the form of a warm airflow), carbon dioxide, ammonia and various nutrients (e.g., derived from mixture of water and livestock manure) that are already being output from the livestock production facility 105. As the airflow is exposed to the algae, it is expected that the algae will absorb a substantial amount of the carbon dioxide and release oxygen, thereby increasing the concentration of oxygen relative to carbon dioxide in the airflow stream.

In the depicted example, the livestock production facility 105 receives back from the algae production module 110 a supply of air with enhanced oxygen levels that may be advantageously supplied to the livestock. The extraction of carbon dioxide and the supply of air with elevated oxygen content are believed likely to enhance and/or generally promote the health and well-being of the livestock, with little additional cost.

The depicted capture of carbon dioxide and ammonia (e.g., NH3) may substantially reduce the rate at which these compounds are released into the atmosphere. The reduction of such emissions, including but not limited to carbon dioxide and ammonia, is believed likely to mitigate some of the smell associated with a livestock production facility 105, and reduce the associated liability or cost of compliance under a carbon regulation scheme. For example, one exemplary effect may be for the algae facility 110 to receive elevated concentrations of CO2, but to emit reduced concentrations of CO2 in the exhaust airflow stream.

In some examples, substantially proximate (e.g., adjacent) co-location of facilities 105, 110 for livestock production and algae production may permit each production facility 105, 110 to substantially directly receive as its input at least some of the outputs of the other production facility. Accordingly, some examples may advantageously capture energy (e.g., heat, airflow kinetic energy) or pollutants (e.g., ammonia, carbon dioxide) being released as waste output from a livestock facility, and use those captured outputs as valuable inputs (e.g., heat, carbon dioxide, nutrients) that are believed to promote algae growth rates. In turn, some of the outputs (e.g., oxygen, edible feed supplements) of the algae production 110 may be beneficially fed directly back to the livestock facility 105, thereby forming a partial closed loop within the facility 100.

Various embodiments may have one or more advantages. For example, some embodiments may be substantially reduce or eliminate storage and/or off-site transportation of inputs (e.g., carbon dioxide, manure) in the production of either livestock or algae. Various embodiments may provide substantial energy savings by re-capturing and re-using the air flow (e.g., kinetic energy) used to regulate temperature in the facility and/or ventilate the livestock facility, FIG. 2 shows a block diagram of an exemplary integrated facility for producing livestock and biologically-derived fuels in a symbiotic manner.

Figure 2:
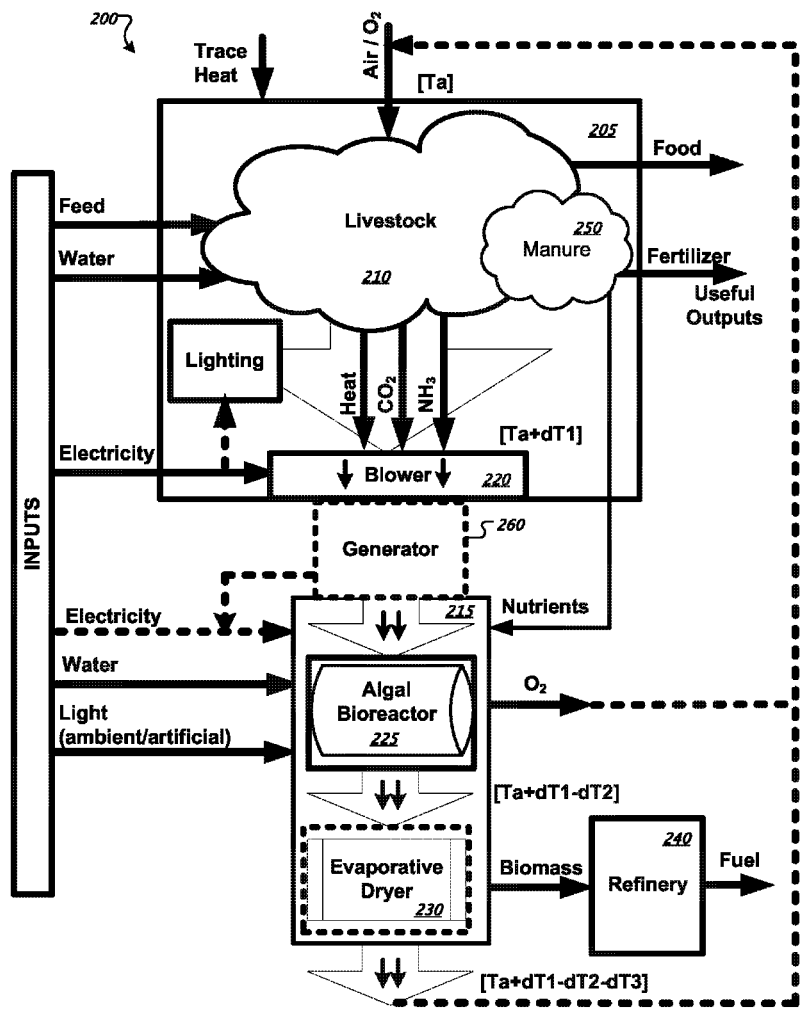
FIG. 2 shows a block diagram of an exemplary integrated facility for producing livestock and biologically-derived fuels in a symbiotic manner.

As depicted in FIG. 2, a facility 200 includes a partially or substantially enclosed housing 205 in which a set of livestock 210 are raised. In close proximity to the housing 205 is an algae production module 215. A forced airflow stream is driven by a blower 220 that, in this example, may provide a negative-to-ambient pressure in the housing 205, and exhaust directly out of the housing 205.

In the depicted example, the algae production module 215 includes an algal bioreactor 225. A duct or other air flow guide (shown as an optional electrical generator) may be provided to direct the exhausted air flow from the blower 220 to the algal bioreactor 225. In some embodiments that use a closed-loop bioreactor, for example, the CO2-rich air exhausted at the blower 220 may be infused into the water that contains the algae by using a bubbling technique. In an open surface reactor (e.g., tank type system), the airflow may be directed to flow over the surface of the algae.

The livestock 210 receive certain inputs (e.g., food, water, light, trace heat, air), and output certain desired "food" or other byproducts that may be readily used (e.g., meat, eggs, fertilizer). The facility 200 further outputs additional byproducts (e.g., heat, CO2, ammonia, and other nutrients that may be extracted, for example, from the forced airflow exhausted by the housing 205, and/or at least a portion of the manure.) In various embodiments, at least a portion of the additional byproducts may be transferred to the algal bioreactor 225 to promote the algae growth. For example, the algal bioreactor 225 may advantageously receive vital inputs that promote the growth of algae, which inputs may include, but are not limited to, waste heat, CO2, and/or NH3, via the forced airflow exhausted from the livestock house 105 by the blower 220.

Certain embodiments may have one or more advantages. For example, symbiotic linkages may be realized by locating a bioreactor in close proximity to the housing for domestic fowl to permit the direct capture and/or transfer of various wasted by-products from the livestock. In some implementations, the smell of ammonia in the airflow exhausted from the livestock house 205 may be substantially attenuated to the extent that the ammonia may be captured or absorbed as a nutrient that promotes algae growth. Some embodiments may capture a substantial portion of heat energy generated by the body heat of the livestock and transferred via the forced airflow. In some examples, such recaptured heat energy may promote faster algae growth rates in the bio-reactor with substantially no additional energy input or costs for heat to maintain a desired temperature of growth medium (e.g., water). Similarly, some embodiments may recapture CO2 generated by the livestock respiration and supply it to stimulate growth of algae. In some implementations, the water input required for the algae reactor may be readily provided by an existing supply of water (e.g., well, holding pond) required for the livestock. Waste water used in the production of livestock (e.g., washing eggs) may, in some embodiments, contain substantial nutrients that may be advantageously recaptured to promote growth in the algae bioreactor.

As depicted in the figure, the exemplary facility 200 further includes an air flow path that provides fluid communication from an exhaust of the blower 220 to an interior volume of the algae growth module 215. In the depicted example, the air flow continues from the algal bioreactor 225 into an evaporative dryer 230. The evaporative dryer may provide a means for passively drying the algae with using the warm flow of air.

In an example implementation, the air flow enters the housing 205 at ambient temperature ([Ta]). The air is warmed in the housing 205 for example by the artificial lighting and body heat to a second temperature ([Ta+dT1]). As the warmed air flow passes through the blower 220, the temperature drops as the air flow is exposed to the bioreactor 225, down to ([Ta+dT1−dT2]). The temperature of the airflow changes again as it passes through the evaporative dryer 230 to ([Ta+dT1−dT2−dT3]). In some implementations, this cooled airflow with reduced CO2 content and enhance O2 content may be optionally recycled back into the housing 205.

The algae production module 215 yields an output of at least partially dried biomass with substantial oil content. This content may be collected and stored for shipment to a refinery 240 for conversion into any of a variety of fuel types.

The livestock 210 produce "food" and manure 250, which may serve as a source of a product for use in fertilizer. The manure 250 is also rich in nutrients that are desirable to grow algae. Accordingly a portion of the manure 250 may be directed to forming, for example, a mixture with water that is rich in nutrients to promote algae growth.

The depicted example flow path includes an optional electric generator 260 (e.g., turbine) be operated to recapture at least some of the (e.g., kinetic) energy supplied by the blower 220. The generator 260 may operate to supply electricity to run a few pumps or instruments (e.g., pressure gauge, CO2 gauge) or to operate the vents.

Figure 3:
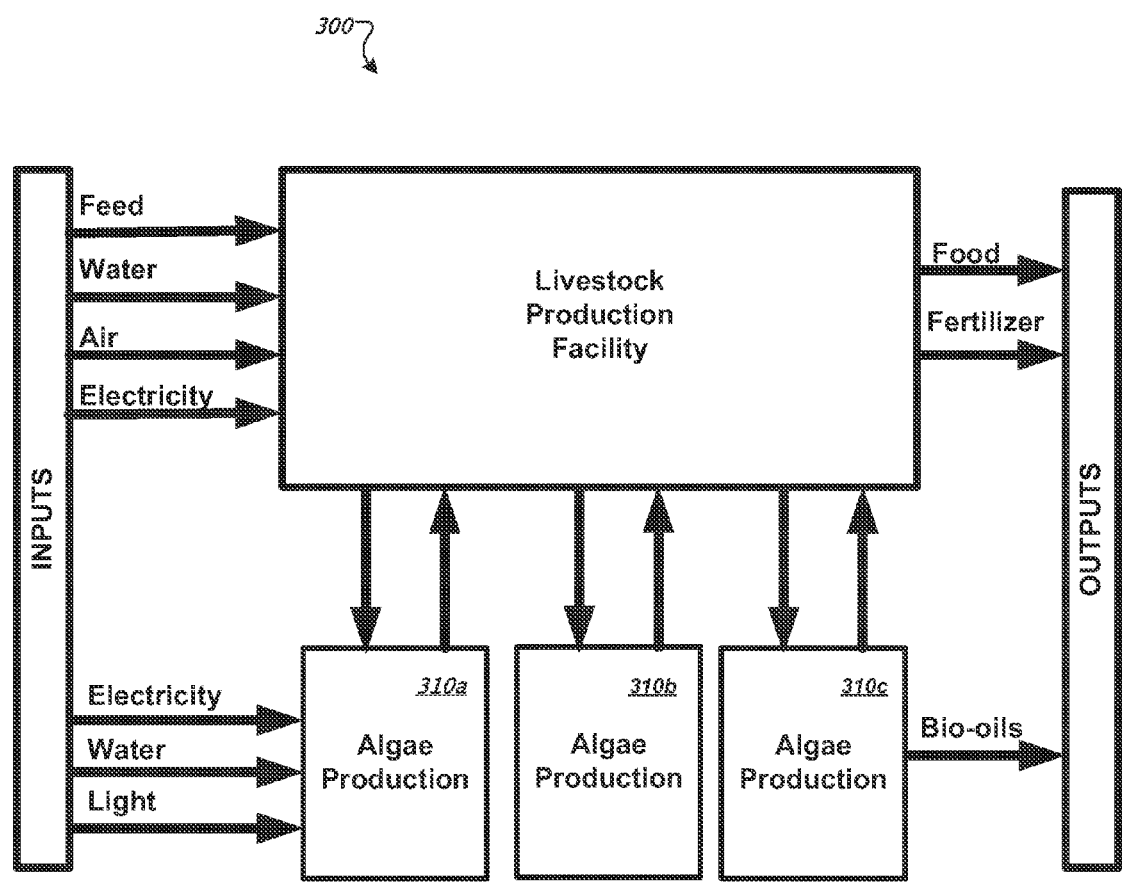
FIG. 3 depicts an exemplary architecture of an integrated facility for livestock and algae production.

FIG. 3 depicts an exemplary architecture of an integrated facility for livestock and algae production. Exemplary algae production modules 310a, 310b, 310c are shown to employ a two-way exchange of materials, such as those that have been described. This example shows that a number of modular bioreactors (e.g., in a shipping container) may be parked next to a livestock house. Selected livestock outputs are transferred to promote algae production, and selected algae outputs are transferred to promote livestock production. In this symbiotic exchange, energy is partially recaptured and recycled so as to lower the cost of production. For example, the recapture heat energy from the livestock may substantially reduce or eliminate the need for additional energy input to maintain the algae at a sufficient temperature to achieve high growth rates.

The close proximity of the livestock and algae production provide for the lowest possible cost to transfer available outputs from one process to the other process.

Although various embodiments have been described with reference to the figures, other embodiments are contemplated. For example, some or all of the algae module 215 may be located within the livestock housing 205. In some examples, the algae module 215 may be arranged on the intake side of the blower 220 so that forced air may be pulled through the algal bioreactor 225.

To raise healthy livestock in a cost-effective and time efficient manner, the housing 205 receives inputs of feed, water, and electricity. In the depicted example, the electricity may be supplied to the at least one blower units 220 arranged to exhaust air from an interior volume of the housing 205. The depicted example also shows that electricity may be used for artificial lighting, which may be manipulated in color and/or intensity to optimize biological development of the livestock, for example. In some examples, the lighting may include LED lighting.

By way of example, and not limitation, the livestock 210 may include various types of fowl, such as chickens, ducks, or turkeys, which may be housed in the housing 205 for the primary purpose of breeding (e.g., egg layers) or for their protein (e.g., broiler chickens). Other livestock, such as cows, horses, sheep, pigs, goats, lamas, emus may be included, singly or in combination, in the livestock population 210.

At least a portion of the evaporative dryer 240 may be on the intake side of the blower 135, in some examples, to pull air warm air through the bioreactor 125 and/or the dryer 135. In some implementations, more than one evaporative dryer 135 may be arranged in series and or parallel in the airflow path driven by the blower 115 as may be needed to implement rapid drying at a desired throughput for the algae.

In one example, oxygen-rich air may be directed via a conduit system to one or more locations in the poultry facility, for example. In one embodiment, an oxygen bar may be established with output ports that exhaust the oxygen-rich flow at a height similar to the water or feed outlets. It is believed that the animals may seek out the oxygen-rich exhaust. It is further contemplated that the oxygen-rich exhaust may be collected, stored and then released in a controlled manner. For example, the oxygen rich release may be controlled temporally in coordination with the availability of other inputs (e.g., food, light, water) to reduce the incidence of fighting over feed, for example. For example, providing oxygen-rich exhaust at a location away from feed pans may reduce crowding at the feed pans. It is believed that in some cases it may be likely that dominant animals may seek out the oxygen if supplied prior to feeding, thereby affording less dominant animals more opportunity to access feed and/or water, and thereby reducing mortality and growth problems.

In some applications, it is believed that controlled elevation of oxygen levels may be beneficial to the animals during certain portions of the schedule, such as in coordination with waking up or with the ramping up of light levels, for example. Accordingly, oxygen level manipulation in selective locations may be beneficial in discouraging and/or attracting the animals to or away from selected locations. By way of example, oxygen rich content may be supplied during selected periods for layers, such as in a desired nesting location during ovation times, which may consequently reduce the number of eggs laid in undesirable locations (e.g., outside of the nest) where egg breakage and spoilage is more likely.

In various examples, a system and a method of using the system for generating biofuels from livestock output is described. One or more algae production facilities may be located within close proximity to a livestock facility. One or more conduits may provide fluid connection between the livestock facility and the algae production facility to transfer livestock output to the algae production facility and algae output to the livestock production facility. Livestock output may promote the growth of algae cells. Algae output may promote the raising and breeding of livestock.

In some embodiments, an algae production facility and a livestock production facility may be located within close proximity of each other and connected by a conduit, such as a pipe. The locations of these facilities allow for the exchange of outputs (e.g., heated air, ammonia vapor, oxygen), which may conventionally treated as waste products.

In some implementations, one or more discrete streams of livestock output may be introduced in a reactor containing algae and an aqueous solution. The algae, water, and livestock output may reside within a reactor for a selected residence time. In some implementations, algae and water in a reactor may be subjected to a continuous stream of livestock output. At least a portion of the algae may be removed for biofuel processing. The remaining portion may be used for growing more algae cells. In some examples, a pump may be used to force livestock output from the livestock production facility into the algae production facility.

What is claimed is:

1. A system for producing algae cells for use in processing biofuel which comprises:
   - a livestock production facility for generating livestock output from livestock consumption of feed and water;
   - an algae production facility located proximate to the livestock production facility, the algae production facility comprising a reaction chamber for growing algae cells using livestock output;
   - a first conduit providing fluid connection between the livestock production facility and the algae production facility, the first conduit defining a passageway comprising an input port through which livestock output is received from the livestock production facility and an output port through which livestock output is discharged into the reaction chamber;
   - a second conduit connecting the livestock production facility and the algae production facility to convey algae output from the algae production facility into the livestock production facility; and
   - means for transferring livestock output from the livestock production facility into the algae production facility through the first conduit,
   - wherein at least a portion of the algae production facility is located within the livestock production facility.

2. The system of claim 1, wherein livestock output comprises manure.

3. The system of claim 1, wherein livestock output comprises ammonia.

4. The system of claim 1, wherein livestock output comprises carbon dioxide.

5. The system of claim 1, wherein livestock output comprises heat.

6. The system of claim 1, wherein livestock output comprises kinetic airflow.

7. The system of claim 1, further comprising means for supplying energy to the system.

8. The system of claim 1, further comprising a housing for storing and shipping the algae production facility, wherein the housing comprises a shipping container.

9. The system of claim 1, wherein the algae output comprises oxygen.

10. A system for producing algae cells for use in processing biofuel which comprises:
    - a livestock production facility for generating livestock output from livestock consumption of feed and water;
    - an algae production facility located proximate to the livestock production facility, the algae production facility comprising a reaction chamber for growing algae cells using livestock output;
    - a first conduit providing fluid connection between the livestock production facility and the algae production facility, the first conduit defining a passageway comprising an input port through which livestock output is received from the livestock production facility and an output port through which livestock output is discharged into the reaction chamber;
    - a second conduit connecting the livestock production facility and the algae production facility to convey algae output from the algae production facility into the livestock production facility; and
    - means for drying algae after being interacted with livestock output to obtain at least partially dried biomass with substantial oil content,
    - wherein at least a portion of the algae production facility is located within the livestock production facility.

11. A method for producing algae cells for use in processing biofuel, the method comprising:
    - providing a system comprising a livestock production facility for generating livestock output from livestock consumption of feed and water, an algae production facility located proximate to the livestock production facility that comprises a reaction chamber for growing algae cells using livestock output, and a conduit connecting the livestock production facility and the algae production facility defining a passageway comprising an input port through which livestock output is received from the livestock production facility and an output port through which livestock output is discharged into the reaction chamber;
    - introducing feed and water into the livestock production facility;
    - generating livestock output based on livestock consumption of feed and water; and,
    - introducing livestock output into the reaction chamber through the conduit to promote the growth of algae cells; and
    - conveying oxygen produced by the algae from the algae production facility into the livestock production facility.

12. The method of claim 11, further comprising drying algae after being interacted with livestock output to obtain at least partially dried biomass with substantial oil content.

13. The method of claim 12, further comprising processing the biomass into a fuel.

14. The method of claim 11, further comprising introducing output from the growth of algae cells from the algae production facility into the livestock production facility.

15. The method of claim 11, further comprising capturing the kinetic airflow available in the livestock production facility to supply energy to operate the algae production facility.

16. The method of claim 15, wherein capturing the kinetic airflow further comprises generating electrical power to operate the algae production facility.

* * * * *